US008093405B2

(12) United States Patent
Carroll et al.

(10) Patent No.: US 8,093,405 B2
(45) Date of Patent: Jan. 10, 2012

(54) FORMATION OF $^{18}$F AND $^{19}$F FLUOROARENES BEARING REACTIVE FUNCTIONALITIES

(75) Inventors: Michael Andrew Carroll, Newcastle upon Tyne (GB); Ran Yan, Newcastle upon Tyne (GB)

(73) Assignee: University of Newcastle Upon Tyne, Newcastle Upon Tyne (GB)

( * ) Notice: Subject to any disclaimer, the term of this patent is extended or adjusted under 35 U.S.C. 154(b) by 112 days.

(21) Appl. No.: 12/467,169

(22) Filed: May 15, 2009

(65) Prior Publication Data

US 2009/0286992 A1 Nov. 19, 2009

Related U.S. Application Data

(60) Provisional application No. 61/053,889, filed on May 16, 2008.

(51) Int. Cl.
*C07D 411/00* (2006.01)
(52) U.S. Cl. ........................................ 548/527; 548/544
(58) Field of Classification Search .................. 548/544, 548/527
See application file for complete search history.

(56) References Cited

FOREIGN PATENT DOCUMENTS

| EP | 0 119 065 | 9/1984 |
|---|---|---|
| EP | 1 471 049 | 10/2004 |
| EP | 1 728 838 | 12/2006 |
| GB | 1 499 508 | 2/1978 |
| JP | 07179511 | * 7/1995 |
| WO | 94/14782 | 7/1994 |
| WO | 02/094319 | 11/2002 |
| WO | 03/064369 | 8/2003 |
| WO | 2005/021472 | 3/2005 |
| WO | 2005/061415 | 7/2005 |
| WO | 2005/097713 | 10/2005 |
| WO | 2007/141529 | 12/2007 |

OTHER PUBLICATIONS

Ross et al. (J. Am. Chem. Soc., 2007, 129; 8018-8025).*
Carroll et al. (J. Labelled Compounds, 2007, 50; 450-451).*
Carroll, Michael A., et. al., "Radical scavengers: A practical solution to the reproducibility issue in the fluoridation of diaryliodonium salts"; Journal of Fluorine Chemistry 128 (2007), pp. 127-132.
Carroll, Michael A., et. al., "Fluoridation of 2-thienyliodonium salts", Journal of Labelled Compounds and Radiopharmaceuticals, J Label Compd Radiopharm 2007; 50: 450-451.
Carroll, Michael A., et. al., Diaryliodonium salts: a solution to 3-(18F)fluoropyridine, Journal of Labelled Compounds and Radiopharmaceuticals, J Label Compd Radiopharm 2007; 50: 452-454.
Dohi, Toshifumi, et. al., "Versatile direct dehydrative approach for diaryliodonium(III) sales in fluoroalcohol media", Chem. Commun., 2007, pp. 4152-4154; with CAPLUS CRN 959773-86-5.

Kokil, P. B., et. al., "Chemistry of Trivalent Iodine: Part i Iodonium Ylides From Phenols", National Chemical Laboratory, Poona 8, Tetrahedron Letters No. 47, pp. 4113-4116, 1977 (Great Britain); with CAPLUS 66166-36-7.
Mading, P., et. al., Module-assisted synthesis of the bifunctional labelling agent N-succinimidyl 4-[18F]fluorobenzoate ([18F]SFB), Science Direct, Applied Radiation and Isotopes 63 (2005); pp. 329-332.
Marik, Jan, et. al., "Fully automated preparation of n.c.a. 4-[18F]fluorobenzoic acid and N-succinimidyl 4-[18F]fluorobenzoate using a Siemens/CTI chemistry process control unit (CPCU)", Science Direct, Applied Radiation and Isotopes 65 (2007); pp. 199-203.
Okarvi, S.M., Recent progress in fluorine-18 labelled peptide radiopharmaceuticals, Cyclotron and Radiopharmaceuticals Department, King Faisal Specialist Hospital and Research Centre, European Journal of Nuclear Medicine vol. 28, No. 7, Jul. 2001 (10 pages).
Ross, Tobias L., et. al., "Nucleophilic 18F-Fluorination of Heteroaromatic Iodonium Salts with No-Carrier-Added [18F]Fluoride", J. Am. Chem.Soc (JACS) Articles 2007, 129, pp. 8018-8025.
Martin-Santamaria, Sonsoles, et. al., "Fluoridation of heteroaromatic iodonium sales—experimental evidence supporting theoretical prediction of the selectivity of the process", The Royal Society of Chemistry 2000, Departmetn of chemistry, Imperial College of Science, Technology and Medicine, London; pp. 649-650.
Tang, G., et. al., "Facile synthesis of N-succinimidyl 4-[18F]fluorobenzoate ([18F]SFB) for protein labeling", Journal of Labelled Compounds and Radiopharmaceuticals, 2008, 51; pp. 68-71.
Vaidyanathan, Ganesan, et. al., "Fluorine-18-Labeled Monoclonal Antibody Fragments: A Potential Approach for Combining Radioimmunoscintigraphy and Positron Emission Tomography", Departments of Radiology and Pathology and the Preuss Laboratory for Brain Tumor Research, Duke University Medical Center, Durham, North Carolina; The Journal of Nuclear Medicine, vol. 33, No. 8, Aug. 1992; pp. 1535-1541.

(Continued)

*Primary Examiner* — Andrew D Kosar
*Assistant Examiner* — Valerie Rodriguez-Garcia
(74) *Attorney, Agent, or Firm* — Osha • Liang LLP

(57) ABSTRACT

An iodonium compound of formula (I):

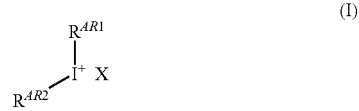

where $R^{AR1}$ is a $C_{5-6}$ aryl group, bearing at least one substituent selected from formyl, thionoacyl, acylamidocarboxy, thionoester, azo, $C_{2-20}$ alkenyl, $C_{2-20}$ alkynyl, and $(CH_2)_nR^C$, where $R^C$ is selected from ether, amino, azo and thioether;
$R^{AR2}$ is a $C_{5-10}$ aryl group, optionally substituted by one or more groups selected from $C_{1-12}$ alkyl, $C_{5-12}$ aryl, $C_{3-12}$ heterocyclyl, ether, thioether, nitro, cyano and halo, and may be linked to a solid support or fluorous tag; and
X is a counteranion.

14 Claims, No Drawings

OTHER PUBLICATIONS

Wester, Hans-Jurgen, et. al., "A Comparative Study of N.C.A. Fluorine-18 Labeling of Proteins via Acylation and Photochemical Conjugation"; Nuclear Medicine & Biology, vol. 23, 1996 (ISSN 0969-8051/96; PH S0969-8051(96) 000017-0); pp. 365-372.

Wust, F., et. al., "Radiolabelling of isopeptide Nε-(γ-glutamyl)-L-lysine by conjugation with N-succinimidyl-4-[18F]fluorobenzoate"; Applied Radiation and Isotopes 59 (2003), Elsevier Ltd.; pp. 43-48.

Zijlstra, S., et. al., "Synthesis and evaluation of a 18F-labelled recombinant annexin-V derivataive, for identification and quantification of apoptotic cells with PET"; Applied Radiation and Isotopes 58 (2003), Elsevier Science Ltd.; pp. 201-207.

Rubenstein, Ken, "Biomarking time"; Chemistry & Industry—Apr. 7, 2008; pp. 23-24.

Yan, Ran, et. al., Poster—"The First Preparatiaon of All Regioisomers of Ethyl [18F]fluorobenzoates"; Newcastle University, School of Natural Sciences (Chemistry); International Isotope Society Meeting, Nov. 1, 2007; Society of Nuclear Medicine Annual Meetings, New Orleans, USA (Jun. 2008) (1 page).

PCT International Search Report and Written Opinion issued Jul. 21, 2009, in International Application No. PCT/GB2009/001262 (14 pages).

Database CA [Online] Chemical Abstracts Service, Columbus, Ohio, US; Ross, Tobias Ludwig; "Direct no-carrier-added 18F-labelling of arenes via nucleophilic substitution on aryl (2-thienyl) iodonium salts"; XP002535690, retrieved from STN Database accession No. 146:379785 abstract & Berichte Des Forschungszentrums Juelich, VOlume Date 2005, JUEL-4200, I-VII, 1-125 CODEN: FJBEE5; ISSN: 0944-2952, 2006. (25 pages).

Ross, Tobias Ludwig; "Direct no-carrier-added 18F-labelling of arenes via nucleophilic substitution on aryl(2-thienyl) iodonium salts"; Berichte des Forschungszentrums Julich; 4200, ISSN 0944-2952, Institut fur Nuklearchemie Jul-4200, D 38 (Diss., Koln, Univ., 2005)—complete article (134 pages).

Carroll, et al., "Fluoridation of 2-thienyliodonium salts"; J. Label. Compd. Radiopharm, vol. 50, 2007, pp. 450-451, XP002535854.

* cited by examiner

FORMATION OF $^{18}$F AND $^{19}$F FLUOROARENES BEARING REACTIVE FUNCTIONALITIES

The present invention relates to methods of forming $^{18}$F and $^{19}$F fluoroarenes bearing reactive functionalities, intermediates in the methods, as well as certain novel compounds which may be produced by the methods.

There is much interest in medicine in the investigation of the properties and actions of biologically active compounds in the body. In particular, the pharmacokinetics and bio-distribution of an active compound in the body is of interest during the development of new drugs and treatments. Investigations can be carried out using non-invasive means by administering labelled active compounds and monitoring their distribution, bioavailability, etc. in the body.

An example of a technique used for such investigations is Positron Emission Tomography (PET) which monitors the distribution of positron emitting isotopes such as $^{11}$C, $^{18}$F, $^{68}$Ga or compounds labelled with the position emitting isotopes in the body. There is therefore a need in the art for methods of manufacturing such labelled compounds.

The introduction of fluorine into aromatic systems is often carried out in the art using electrophilic fluorine reagents (F$^+$). Examples of such electrophilic reagents include $F_2$, $XeF_2$, AcOF, $CF_3COOF$, Selectfluor™ and N-fluorosulfonimides. Synthesis of these radiolabelled reagents is problematic however as the source of the positron emitting isotope $[^{18}F]F_2$ used to produce these reagents can only be obtained with a relatively low specific activity. $[^{18}F]$Fluoride may be obtained in much higher amounts and in much higher specific radioactivity and is therefore the preferred reagent for the introduction of fluorine-18.

A particular compound of interest containing $^{18}$F is N-succinimidyl 4-$[^{18}F]$fluorobenzoate ($[^{18}F]$SFB). This has been shown to be a suitable acylation agent for radiolabelling of peptides, proteins, oligonucleotides and antibodies (Vaidyanathan, G., et al., *J. Nucl. Med.* 33, 1535-1541 (1992); Wester, H. J., et al., *Nucl. Med. Biol.*, 23, 365-372 (1996); Wüst, F., et al., *Appl. Radiat. Isot.*, 59, 43-48 (2003); Zijlstra, S., et al., Appl. Radiat. Isot. 58, 201-207 (2003)). Such bioactive compounds when labelled with a $[^{18}F]$fluorobenzoyl group can be useful radiotracers for in vivo studies of physiological processes by positron emission tomography (PET).

The synthesis of $^{18}$F and $^{19}$F fluoroarenes, using fluoride, bearing reactive functionalities, including SFB, is problematic, as the reactive functionality provides an alternative (usually preferred) reaction site for the fluoride. The result is that the process typically generates a complex mixture of products, causing the isolation of the desired material to be difficult. Given the use of a short lived radioisotope compounds ($^{18}$F, half-life 109.7 min) this lack of selectivity presents a serious problem, as time consuming conventional purification procedures cannot be employed. However, the purity of the final compound is essential to allow direct and immediate administration of the radiotracer to a patient. In addition, alternative reaction pathways for the radioisotope (via the reactive functionality) greatly reduces the radiochemical and specific activity of the target material. To over come this, traditional approaches to fluorine-18 labelled materials bearing reactive functionalities involve multi-step, multi-pot procedures where the reactive functionality is typically introduced after the radioisotope. These additional reaction and purification steps take significant time given the short half-life of the radioisotope and are therefore undesirable. The additional complexity associated with multi-step reaction sequences using short-lived isotopes increases the hazards to the operator, is detrimental to both the radiochemical yield and specific activity of the product and also limits the opportunities for automated production of labelled material using commercial apparatus. In turn these constraints greatly restrict the translation of synthetic methods to GMP production of radiopharmaceuticals for clinical use.

To address these limitations the present inventors have developed a single-step single-pot method of synthesising $^{18}$F and $^{19}$F fluoroarenes bearing reactive functionalities from a biaryliodonium salt intermediate.

Accordingly, a first aspect of the present invention provides an iodonium compound of formula (I):

where $R^{AR1}$ is a $C_{5-6}$ aryl group, bearing at least one substituent selected from formyl, thionoacyl, acylamidocarboxy, thionoester, azo, $C_{2-20}$ alkenyl, $C_{2-20}$ alkynyl, and $(CH_2)_n R^C$, where $R^C$ is selected from ether, amino, azo and thioether;

$R^{AR2}$ is a $C_{5-10}$ aryl group, optionally substituted by one or more groups selected from $C_{1-12}$ alkyl, $C_{5-12}$ aryl, $C_{3-12}$ heterocyclyl, ether, thioether, nitro, cyano and halo, and may be linked to a solid support or fluorous tag (which can be used to expediate purification of the target material);

X is a counteranion.

A second aspect of the invention provides a method of synthesising a compound of formula II:

by fluoridating a compound of formula I.

In some embodiments, the fluoro group is $^{18}$F. The $^{18}$F will usually have an abundance of at least 90% or 95% relative to $^{19}$F. In some embodiments, the $^{18}$F will have an abundance of 99% or even 99.9%.

A third aspect of the invention provides novel compounds of formula II.

A fourth aspect of the present invention provides a method of synthesising a compound of formula I comprising the step of reacting a compound of formula IIIa or IIIb:

with a compound of formula IVa or IVb:

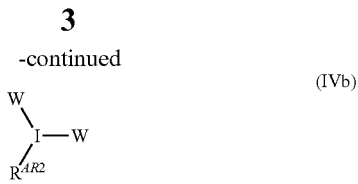

(IVb)

wherein Q is SnR$_3$, B(OH)$_2$ or B(OR)$_2$, where R is C$_{1-7}$ alkyl; and

W is OCOR$^W$ or halo (e.g. Cl), where R$^W$ is C$_{1-4}$ alkyl (including fluoroalkyl).

A further aspect of the present invention provides a compound of formula (II) obtained by the method of the second aspect.

Definitions

Solid support: The term "solid support" as used herein, pertains to any suitable solid-phase support which is insoluble in any solvents to be used in the processes of the invention but to which the linker can be covalently bound. Examples of suitable solid support include polymers such as polystyrene (which may be block grafted, for example with polyethylene glycol), polyacrylamide, or polypropylene or glass or silicon coated with such a polymer. The solid support may be in the form of small discrete particles such as beads or pins, or as a coating on the inner surface of a cartridge or on a microfabricated vessel.

Fluorous tag: The term "fluorous tag" as used herein, pertains to a perfluoroalkyl group having from 6 to 20 carbon atoms, i.e. perfluoroC$_{6-20}$ alkyl. Examples of fluorous tags include, but are not limited to, —C$_6$F$_{13}$, —C$_5$F$_{11}$, —C$_8$F$_{17}$ and C$_{10}$F$_{21}$. Examples of such fluorous tags are well known to those skilled in the art.

Linker: The term "linker" may be any suitable organic group which serves to space the reactive site sufficiently from the solid support structure or fluorous tag so as to maximise reactivity. The linker will be a divalent moiety and can be derived in particular from C$_{1-20}$ alkyl and C$_{1-20}$ alkoxy groups. The linker may be substituted or unsubstituted. The linker may also by derived from polyethylene glycol, and thus be of the formula (—C$_2$H$_4$—O—)$_n$, where n is from 2 to 10. Examples of such linkers are well known to those skilled in the art of solid-phase chemistry.

Alkyl: The term "alkyl" as used herein, pertains to a monovalent moiety obtained by removing a hydrogen atom from a carbon atom of a hydrocarbon compound having from 1 to 20 carbon atoms (unless otherwise specified), which may be aliphatic or alicyclic, and which may be saturated or unsaturated (e.g. partially unsaturated, fully unsaturated). Thus, the term "alkyl" includes the sub-classes alkenyl, alkynyl, cycloalkyl, cycloalkyenyl, cycloalkynyl, etc., discussed below.

In the context of alkyl groups, the prefixes (e.g. C$_{1-4}$, C$_{1-7}$, C$_{2-7}$, C$_{3-7}$, etc.) denote the number of carbon atoms, or range of number of carbon atoms. For example, the term "C$_{1-4}$ alkyl", as used herein, pertains to an alkyl group having from 1 to 4 carbon atoms. Examples of groups of alkyl groups include C$_{1-4}$ alkyl ("lower alkyl") and C$_{1-7}$ alkyl. Note that the first prefix may vary according to other limitations; for example, for unsaturated alkyl groups, the first prefix must be at least 2; for cyclic alkyl groups, the first prefix must be at least 3; etc.

Examples of (unsubstituted) saturated alkyl groups include, but are not limited to, methyl (C$_1$), ethyl (C$_2$), propyl (C$_3$), butyl (C$_4$), pentyl (C$_5$), hexyl (C$_6$), heptyl (C$_7$), octyl (C$_8$), nonyl (C$_9$), decyl (C$_{10}$), undecyl (C$_{11}$) and dodecyl (C$_{12}$).

Examples of (unsubstituted) saturated linear alkyl groups include, but are not limited to, methyl (C$_1$), ethyl (C$_2$), n-propyl (C$_3$), n-butyl (C$_4$), n-pentyl (amyl) (C$_5$), n-hexyl (C$_6$), and n-heptyl (C$_7$).

Examples of (unsubstituted) saturated branched alkyl groups include iso-propyl (C$_3$), iso-butyl (C$_4$), sec-butyl (C$_4$), tert-butyl (C$_4$), iso-pentyl (C$_5$), and neo-pentyl (C$_5$).

Alkenyl: The term "alkenyl", as used herein, pertains to an alkyl group having one or more carbon-carbon double bonds. Examples of groups of alkenyl groups include C$_{2-4}$ alkenyl, C$_{2-7}$ alkenyl and C$_{2-12}$ alkenyl.

Examples of (unsubstituted) unsaturated alkenyl groups include, but are not limited to, ethenyl (vinyl, —CH═CH$_2$), 1-propenyl (—CH═CH—CH$_3$), 2-propenyl (allyl, —CH—CH═CH$_2$), isopropenyl (1-methylvinyl, —C(CH$_3$)═CH$_2$), butenyl (C$_4$), pentenyl (C$_5$), and hexenyl (C$_6$).

Alkynyl: The term "alkynyl", as used herein, pertains to an alkyl group having one or more carbon-carbon triple bonds. Examples of groups of alkynyl groups include C$_{2-4}$ alkynyl, C$_{2-7}$ alkynyl and C$_{2-12}$ alkynyl.

Examples of (unsubstituted) unsaturated alkynyl groups include, but are not limited to, ethynyl (ethinyl, —C≡CH) and 2-propynyl (propargyl, —CH$_2$—C≡CH).

Cycloalkyl: The term "cycloalkyl", as used herein, pertains to an alkyl group which is also a cyclyl group; that is, a monovalent moiety obtained by removing a hydrogen atom from an alicyclic ring atom of a carbocyclic ring of a carbocyclic compound, which carbocyclic ring may be saturated or unsaturated (e.g. partially unsaturated, fully unsaturated), which moiety has from 3 to 7 carbon atoms (unless otherwise specified), including from 3 to 7 ring atoms. Thus, the term "cycloalkyl" includes the sub-classes cycloalkenyl and cycloalkynyl. Preferably, each ring has from 3 to 7 ring atoms. Examples of groups of cycloalkyl groups include C$_{3-7}$ cycloalkyl and C$_{3-12}$ cycloalkyl.

Examples of cycloalkyl groups include, but are not limited to, those derived from:

saturated monocyclic hydrocarbon compounds:
cyclopropane (C$_3$), cyclobutane (C$_4$), cyclopentane (C$_5$), cyclohexane (C$_6$), cycloheptane (C$_7$), methylcyclopropane (C$_4$), dimethylcyclopropane (C$_5$), methylcyclobutane (C$_5$), dimethylcyclobutane (C$_6$), methylcyclopentane (C$_6$), dimethylcyclopentane (C$_7$), methylcyclohexane (C$_7$), dimethylcyclohexane (C$_8$) and menthane (C$_{10}$);

unsaturated monocyclic hydrocarbon compounds:
cyclopropene (C$_3$), cyclobutene (C$_4$), cyclopentene (C$_5$), cyclohexene (C$_6$), methylcyclopropene (C$_4$), dimethylcyclopropene (C$_5$), methylcyclobutene (C$_5$), dimethylcyclobutene (C$_6$), methylcyclopentene (C$_6$), dimethylcyclopentene (C$_7$), methylcyclohexene (C$_7$) and dimethylcyclohexene (C$_8$);

saturated polycyclic hydrocarbon compounds:
thujane (C$_{10}$), carane (C$_{10}$), pinane (C$_{10}$), bornane (C$_{10}$), norcarane (C$_7$), norpinane (C$_7$), norbornane (C$_7$), adamantane (C$_{10}$) and decalin (decahydronaphthalene) (C$_{10}$); and unsaturated polycyclic hydrocarbon compounds:
camphene (C$_{10}$), limonene (C$_{10}$) and pinene (C$_{10}$).

Heterocyclyl: The term "heterocyclyl", as used herein, pertains to a monovalent moiety obtained by removing a hydrogen atom from a ring atom of a heterocyclic compound, which moiety has from 3 to 7 ring atoms (unless otherwise specified), of which from 1 to 4 are ring heteroatoms. Preferably, each ring has from 3 to 7 ring atoms, of which from 1 to 4 are ring heteroatoms.

In this context, the prefixes (e.g. C$_{3-7}$, C$_{5-6}$, etc.) denote the number of ring atoms, or range of number of ring atoms, whether carbon atoms or heteroatoms. For example, the term "C$_{5-6}$heterocyclyl", as used herein, pertains to a heterocyclyl group having 5 or 6 ring atoms. Examples of groups of heterocyclyl groups include $C_{3-7}$ heterocyclyl, $C_{5-7}$ heterocyclyl, and $C_{5-6}$ heterocyclyl.

Examples of monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted (non-aromatic) monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

Spiro-$C_{3-7}$ cycloalkyl or heterocyclyl: The term "spiro $C_{3-7}$ cycloalkyl or heterocyclyl" as used herein, refers to a $C_{3-7}$ cycloalkyl or $C_{3-7}$ heterocyclyl ring joined to another ring by a single atom common to both rings.

$C_{5-20}$ aryl: The term "$C_{5-20}$ aryl" as used herein, pertains to a monovalent moiety obtained by removing a hydrogen atom from an aromatic ring atom of a $C_{5-20}$ aromatic compound, said compound having one ring, or two or more rings (e.g., fused), and having from 5 to 20 ring atoms, and wherein at least one of said ring(s) is an aromatic ring. Preferably, each ring has from 5 to 7 ring atoms.

The ring atoms may be all carbon atoms, as in "carboaryl groups" in which case the group may conveniently be referred to as a "$C_{5-20}$ carboaryl" group.

Examples of $C_{5-20}$ aryl groups which do not have ring heteroatoms (i.e. $C_{5-20}$ carboaryl groups) include, but are not limited to, those derived from benzene (i.e. phenyl) ($C_6$), naphthalene ($C_{10}$), anthracene ($C_{14}$), phenanthrene ($C_{14}$), and pyrene ($C_{16}$).

Alternatively, the ring atoms may include one or more heteroatoms, including but not limited to oxygen, nitrogen, and sulfur, as in "heteroaryl groups". In this case, the group may conveniently be referred to as a "$C_{5-20}$ heteroaryl" group, wherein "$C_{5-20}$" denotes ring atoms, whether carbon atoms or heteroatoms. Preferably, each ring has from 5 to 7 ring atoms, of which from 0 to 4 are ring heteroatoms.

Examples of $C_{5-20}$ heteroaryl groups include, but are not limited to, $C_5$ heteroaryl groups derived from furan (oxole), thiophene (thiole), pyrrole (azole), imidazole (1,3-diazole), pyrazole (1,2-diazole), triazole, oxazole, isoxazole, thiazole, isothiazole, oxadiazole, tetrazole and oxatriazole; and $C_6$ heteroaryl groups derived from isoxazine, pyridine (azine), pyridazine (1,2-diazine), pyrimidine (1,3-diazine; e.g., cytosine, thymine, uracil), pyrazine (1,4-diazine) and triazine.

The heteroaryl group may be bonded via a carbon or hetero ring atom.

Examples of $C_{5-20}$ heteroaryl groups which comprise fused rings, include, but are not limited to, $C_9$ heteroaryl groups derived from benzofuran, isobenzofuran, benzothiophene, indole, isoindole; $C_{10}$ heteroaryl groups derived from quinoline, isoquinoline, benzodiazine, pyridopyridine; $C_{14}$ heteroaryl groups derived from acridine and xanthene.

The above alkyl, heterocyclyl, and aryl groups, whether alone or part of another substituent, may themselves optionally be substituted with one or more groups selected from themselves and the additional substituents listed below.

Azo: —$N_3$

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.

Nitro: —$NO_2$.

Cyano (nitrile, carbonitrile): —CN.

Acyl (keto): —C(=O)R, wherein R is an acyl substituent, for example, H, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)$CH_3$ (acetyl), —C(=O)$CH_2CH_3$ (propionyl), —C(=O)C($CH_3$)$_3$ (butyryl), and —C(=O)Ph (benzoyl, phenone).

Thionoacyl: —C(=S)R, where R is a thionoacyl substituent, for example, H, a $C_{1-7}$ alkyl group (also referred to as $C_{1-7}$ alkylthionoacyl), a $C_{3-20}$ heterocyclyl group (also referred to as $C_{3-20}$ heterocyclylthionoacyl), or a $C_{5-20}$ aryl group (also referred to as $C_{5-20}$ arylthionoacyl), preferably a $C_{1-7}$ alkyl group. Examples of thionoacyl groups include, but are not limited to, —C(=S)$CH_3$, —C(=S)$CH_2CH_3$, —C(=S)C($CH_3$)$_3$, and —C(=S)Ph.

Formyl (carbaldehyde, carboxaldehyde): —C(=O)H.

Carboxy (carboxylic acid): —COOH.

Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group (a $C_{1-7}$ alkyl ester). Examples of ester groups include, but are not limited to, —C(=O)$OCH_3$, —C(=O)$OCH_2CH_3$, —C(=O)OC($CH_3$)$_3$, and —C(=O)OPh.

Thionoester: —C(=S)OR, wherein R is an thionoester substituent, for example, a $C_{1-7}$ alkyl group, a $C_{3-20}$ heterocyclyl group, or a $C_{5-20}$ aryl group, preferably a $C_{1-7}$ alkyl group (a $C_{1-7}$ alkyl ester). Examples of ester groups include, but are not limited to, —C(=S)$OCH_3$, —C(=S)$OCH_2CH_3$, —C(=S)OC($CH_3$)$_3$, and —C(=S)OPh.

Amido (carbamoyl, carbamyl, aminocarbonyl, carboxamide): —C(=O)$NR^1R^2$, wherein $R^1$ and $R^2$ are independently amino substituents, as defined for amino groups. Examples of amido groups include, but are not limited to, —C(=O)$NH_2$, —C(=O)$NHCH_3$, —C(=O)N($CH_3$)$_2$, —C(=O)$NHCH_2CH_3$, and —C(=O)N($CH_2CH_3$)$_2$, as well as amido groups in which $R^1$ and $R^2$, together with the nitrogen atom to which they are attached, form a heterocyclic structure as in, for example, piperidinocarbonyl, morpholinocarbonyl, thiomorpholinocarbonyl, and piperazinylcarbonyl.

Amino: —$NR^1R^2$, wherein $R^1$ and $R^2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, $R^1$ and $R^2$, taken together with the nitrogen atom to which they are attached, form a heterocyclic ring having from 4 to 8 ring atoms. Examples of amino groups include, but are not limited to, —$NH_2$, —$NHCH_3$, —$NHCH(CH_3)_2$, —$N(CH_3)_2$, —$N(CH_2CH_3)_2$, and —NHPh. Examples of cyclic amino groups include, but are not limited to, aziridinyl, azetidinyl, pyrrolidinyl, piperidino, piperazinyl, perhydrodiazepinyl, morpholino, and thiomorpholino. The cylic amino groups may be substituted on their ring by any of the substituents defined here, for example carboxy, carboxylate and amido.

Acylamido (acylamino): —$NR^1C(=O)R^2$, wherein $R^1$ is an amide substituent, for example, hydrogen, a $C_{1-7}$ alkyl group, a $C_{3-20}$ heterocyclyl group, or a $C_{5-20}$ aryl group, preferably H or a $C_{1-7}$ alkyl group, most preferably H, and $R^2$ is an acyl substituent, for example, a $C_{1-7}$ alkyl group, a $C_{3-20}$ heterocyclyl group, or a $C_{5-20}$ aryl group, preferably a $C_{1-7}$ alkyl group. Examples of acylamide groups include, but are not limited to, —$NHC(=O)CH_3$, —$NHC(=O)CH_2CH_3$, and —$NHC(=O)Ph$. $R^1$ and $R^2$ may together form a cyclic structure, as in, for example, succinimidyl, maleimidyl, and phthalimidyl:

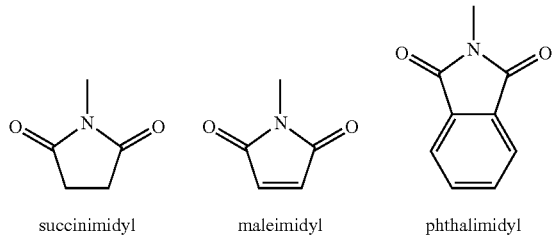

succinimidyl    maleimidyl    phthalimidyl

Acylamidocarboxy: —$C(=O)ONR^1C(=O)R^2$, wherein $R^1$ is an amide substituent, for example, hydrogen, a $C_{1-7}$ alkyl group, a $C_{3-20}$ heterocyclyl group, or a $C_{5-20}$ aryl group, preferably H or a $C_{1-7}$ alkyl group, most preferably H, and $R^2$ is an acyl substituent, for example, a $C_{1-7}$ alkyl group, a $C_{3-20}$ heterocyclyl group, or a $C_{5-20}$ aryl group, preferably a $C_{1-7}$ alkyl group. Examples of acylamidocarboxy groups include, but are not limited to, —$C(=O)ONHC(=O)CH_3$, —$C(=O)ONHC(=O)CH_2CH_3$, and —$C(=O)ONHC(=O)Ph$. $R^1$ and $R^2$ may together form a cyclic structure, as in, for example, succinimidylcarboxy, maleimidylcarboxy, and phthalimidylcarboxy:

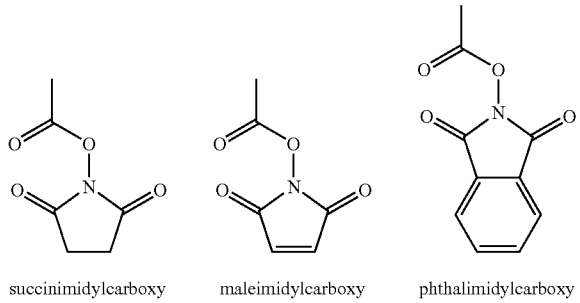

succinimidylcarboxy    maleimidylcarboxy    phthalimidylcarboxy

Ureido: —$N(R^1)CONR^2R^3$ wherein $R^2$ and $R^3$ are independently amino substituents, as defined for amino groups, and $R^1$ is a ureido substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group. Examples of ureido groups include, but are not limited to, —$NHCONH_2$, —$NHCONHMe$, —$NHCONHEt$, —$NHCONMe_2$, —$NHCONEt_2$, —$NMeCONH_2$, —$NMeCONHMe$, —$NMeCONHEt$, —$NMeCONMe_2$, —$NMeCONEt_2$ and —$NHC(=O)NHPh$.

Acyloxy (reverse ester): —$OC(=O)R$, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —$OC(=O)CH_3$ (acetoxy), —$OC(=O)CH_2CH_3$, —$OC(=O)C(CH_3)_3$, —$OC(=O)Ph$, —$OC(=O)C_6H_4F$, and —$OC(=O)CH_2Ph$.

Thiol: —SH.

Thioether (sulfide): —SR, wherein R is a thioether substituent, for example, a $C_{1-7}$ alkyl group (also referred to as a $C_{1-7}$ alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —$SCH_3$ and —$SCH_2CH_3$.

Sulfoxide (sulfinyl): —$S(=O)R$, wherein R is a sulfoxide substituent, for example, a $C_{1-7}$ alkyl group, a $C_{3-20}$ heterocyclyl group, or a $C_{5-20}$ aryl group, preferably a $C_{1-7}$ alkyl group. Examples of sulfoxide groups include, but are not limited to, —$S(=O)CH_3$ and —$S(=O)CH_2CH_3$.

Sulfonyl (sulfone): —$S(=O)_2R$, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group. Examples of sulfone groups include, but are not limited to, —$S(=O)_2CH_3$ (methanesulfonyl, mesyl), —$S(=O)_2CF_3$, —$S(=O)_2CH_2CH_3$, and 4-methylphenylsulfonyl (tosyl).

Thioamido (thiocarbamyl): —$C(=S)NR^1R^2$, wherein $R^1$ and $R^2$ are independently amino substituents, as defined for amino groups. Examples of amido groups include, but are not limited to, —$C(=S)NH_2$, —$C(=S)NHCH_3$, —$C(=S)N(CH_3)_2$, and —$C(=S)NHCH_2CH_3$.

Sulfonamino: —$NR^1S(=O)_2R$, wherein $R^1$ is an amino substituent, as defined for amino groups, and R is a sulfonamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfonamino groups include, but are not limited to, —$NHS(=O)_2CH_3$, —$NHS(=O)_2Ph$ and —$N(CH_3)S(=O)_2C_6H_5$.

Siloxy (silyl ether): —$OSiR_3$, where R is H or a $C_{1-7}$ alkyl group. Examples of silyloxy groups include, but are not limited to, —$OSiH_3$, —$OSiH_2(CH_3)$, —$OSiH(CH_3)_2$, —$OSi(CH_3)_3$, —$OSi(Et)_3$, —$OSi(iPr)_3$, —$OSi(tBu)(CH_3)_2$, and —$OSi(tBu)_3$.

As mentioned above, the groups that form the above listed substituent groups, e.g. $C_{1-7}$ alkyl, $C_{3-20}$ heterocyclyl and $C_{5-20}$ aryl, may themselves be substituted. Thus, the above definitions cover substituent groups which are substituted.

All the documents referenced herein are incorporated by reference.

Further Preferences and Embodiments

First Aspect $R^{AR1}$ $R^{AR1}$ is a $C_{5-6}$ aryl group, bearing at least one substituent selected from formyl, thionoacyl, acylamidocarboxy, thionoester, azo, $C_{2-20}$ alkenyl, $C_{2-20}$ alkynyl, and $(CH_2)_nR^C$, where $R^C$ is selected from ether, amino, azo and thioether.

In some embodiments, the $C_{5-6}$ aryl group may bear a single substituent. In other embodiments, the $C_{5-6}$ aryl group may bear two, three or four substituents.

If $R^{AR1}$ is a heteroaryl group it may be selected from a $C_5$ heteroaryl group derived from: furan (oxole), thiophene (thiole), pyrrole (azole), imidazole (1,3-diazole), pyrazole (1,2-diazole), triazole, oxazole, isoxazole, thiazole, isothiazole, oxadiazole, tetrazole and oxatriazole; or from a $C_6$ heteroaryl group derived from: isoxazine, pyridine (azine), pyridazine (1,2-diazine), pyrimidine (1,3-diazine; e.g., cytosine, thymine, uracil), pyrazine (1,4-diazine) and triazine.

If $R^{AR1}$ is a carboaryl group, it is phenyl. In these embodiments, $R^{AR1}$ can be represented as:

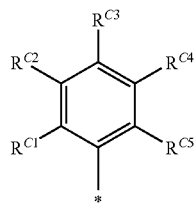

wherein each of $R^{C1}$, $R^{C2}$, $R^{C3}$, $R^{C4}$ and $R^{C5}$ are selected from H and formyl, thionoacyl, acylamidocarboxy, thionoester, azo, $C_{2-20}$ alkenyl, $C_{2-20}$ alkynyl, and $(CH_2)_n R^C$, where $R^C$ is selected from ether, amino, azo and thioether, provided that at least one of $R^{C1}$, $R^{C2}$, $R^{C3}$, $R^{C4}$ and $R^{C5}$ is not H.

In some embodiments, which may be preferred, one of $R^{C1}$, $R^{C2}$, $R^{C3}$, $R^{C4}$ and $R^{C5}$ is selected from formyl, thionoacyl, acylamidocarboxy, thionoester and $(CH_2)_n R^C$, where $R^C$ is selected from ether, azo, amino and thioether, whilst the remaining groups are H. In other embodiments, two, three or four of $R^{C1}$, $R^{C2}$, $R^{C3}$, $R^{C4}$ and $R^{C5}$ is selected from formyl, thionoacyl, acylamidocarboxy, thionoester and $(CH_2)_n R^C$, where $R^C$ is selected from ether, azo, amino and thioether, whilst the remaining groups are H.

The substituents for $R^{AR1}$ may, in some embodiments, be selected from formyl, carboxy, acylamidocarboxy (e.g. $CO_2N(COCH_2)_2$), $CH_2OH$ and $CH_2NH_2$.

In some embodiments, $R^{AR1}$ bears a single substituent that is an acylamidocarboxy group. Of particular interest are groups in which the amide and acyl substituent form a cyclic structure, for example:

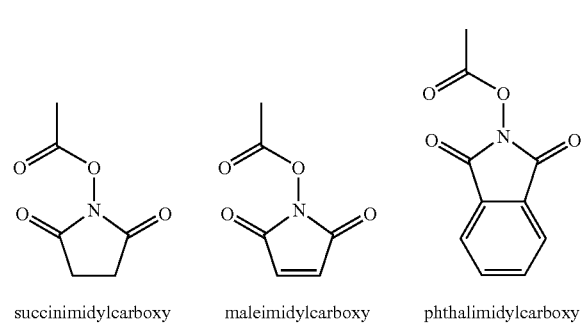

succinimidylcarboxy    maleimidylcarboxy    phthalimidylcarboxy

Of these groups, succinimidylcarboxy may be preferred.

If $R^{AR1}$ in these embodiments is phenyl and its sole substituent is succinimidylcarboxy, then the compound produced by fluoridation is N-succinimidyl-fluorobenzoate, and may be N-succinimidyl-2-fluorobenzoate, N-succinimidyl-3-fluorobenzoate or N-succinimidyl-4-fluorobenzoate in which the fluoro group may be labelled or unlabelled.

$$\frac{R^{AR2}}{R^{AR2}}$$

is a $C_{5-10}$ aryl group that is optionally substituted by one or more groups selected from $C_{1-12}$ alkyl, $C_{5-12}$ aryl, $C_{3-12}$ heterocyclyl, ether, thioether, nitro, cyano and halo. $R^{AR2}$ may be linked to a solid support or fluorous tag.

If $R^{AR2}$ is a heteroaryl group it may be selected from a $C_5$ heteroaryl group derived from: furan (oxole), thiophene (thiole), pyrrole (azole), imidazole (1,3-diazole), pyrazole (1,2-diazole), triazole, oxazole, isoxazole, thiazole, isothiazole, oxadiazole, tetrazole and oxatriazole; or from a $C_6$ heteroaryl group derived from: isoxazine, pyridine (azine), pyridazine (1,2-diazine), pyrimidine (1,3-diazine; e.g., cytosine, thymine, uracil), pyrazine (1,4-diazine) and triazine. Of these thiophenyl and furanyl may be preferred, and thiophenyl (e.g. thiophen-2-yl, thiophen-3-yl) may be more preferred. These groups may be substituted or unsubstituted. In some embodiments, it is preferred that they are not substituted.

If $R^{AR2}$ is a carboaryl group, it is phenyl.

Preferred substituents for $R^{AR2}$ may include ethers, thioethers and amines. Of these ethers (for example, $C_{1-7}$ alkoxy (methoxy, ethoxy)) may be preferred.

Without wishing to be bound by theory, having $R^{AR2}$ as a $C_5$ heteroaryl group results in a particularly stable iodonium salt of formula I, which when fluorinated under the reaction conditions described herein produces a high yield. This is though to be especially the case when the fluorination is by $^{18}F$ which proceeds with a good radiochemical yield.

X

X is a counteranion. It may be selected from $CF_3COO$, TsO, MsO, NsO, TfO, $NO_3$, Br, Cl and $SO_4$. It may also be selected from $BAr_4$, where Ar represents a $C_{5-20}$ aryl group, such as a $C_{5-7}$ aryl group (e.g. phenyl, tolyl). The aryl group may itself be substituted, as described above.

In some embodiments, the counteranion may be trifluoroacetate, trifluoromethane sulfonate or tosyl. Of these trifluoroacetate is the most preferred, with TfO also being preferred.

Second Aspect

The second aspect of the invention provides a method of synthesising a compound of formula II:

$$R^{AR} \atop | \atop F$$

by fluoridating a compound of formula I. The fluoridation can involve the introduction of $^{18}F$ or $^{19}F$. The source of fluoride can provide fluoride as labelled (for example $[^{18}F]F^-$ or unlabelled fluoride. Examples of fluoride sources are NaF, KF, CsF, tetraalkylammonium fluoride, or tetraalkylphosphonium fluoride. Examples of $[^{18}F]$ fluoride sources include $Na^{18}F$, $K^{18}F$, $Cs^{18}F$, tetraalkylammonium $[^{18}F]$ fluoride, or tetraalkylphosphonium $[^{18}F]$ fluoride. To increase the reactivity of the fluoride, a phase transfer catalyst such as an aminopolyether or crown ether for example, 4,7,13,16,21,24 hexaoxa-1,10-diazabicyclo[8,8,8] hexacosane (Kryptofix 2.2.2) may be added and the reaction performed in a suitable solvent.

These conditions give reactive fluoride ions. Optionally, a free radical trap may be used to improve fluoridation yields, as described in WO 2005/061415. The term "free radical trap" is defined as any agent that interacts with free radicals and inactivates them. A suitable free radical trap for this purpose may be selected from 2,2,6,6-Tetramethylpiperidine-N-Oxide (TEMPO), 1,2-diphenylethylene (DPE), ascorbate, para-amino benzoic acid (PABA), a-tocopherol, hydroquinone, di-t-butyl phenol, β-carotene and gentisic acid. Preferred free radical traps for use In the method of the invention are TEMPO and DPE, with TEMPO being most preferred.

The treatment with fluoride may be effected in the presence of a suitable organic solvent such; as acetonitrile, dimethylformamide, dimethylsulphoxide, dimethylacetamide, tetrahydrofuran, dioxan, 1,2-dimethoxyethane, sulpholane, N-methylpyrolidininone, or in an ionic liquid such as an imidazolium derivative (for example 1-ethyl-3-methylimidazolium hexafluorophosphate), a pyridinium derivative (for example, 1-butyl-4methylpyridinium tetrafluoroborate), a phosphonium compound, or tetralkylammonium compound at a non-extreme temperature, for example, 15° C. to 150° C., preferably at elevated temperature, such as 80° C. to 150° C., for example around 110° C. Other possible organic solvents include tert-amyl alcohol, trifluoroethanol and hexfluoroisopropanol. The reaction may be carried out at upto 250° C.

In one aspect of the invention, the solvent used is dry, meaning that the level of water present is 1000 ppm or less, more suitably 600 ppm or less, and preferably 100 ppm or less.

Third Aspect

N-succinimidyl-2-fluorobenzoate, N-succinimidyl-3-fluorobenzoate, N-succinimidyl-2-[$^{18}$F]fluorobenzoate and N-succinimidyl-3-[$^{18}$F]fluorobenzoate may be embodiments of the third aspect of the invention.

Fourth Aspect

W may be acetate or trifluoroacetate.

Q may be SnBu$_3$ or SnMe$_3$.

The embodiments and preferences expressed above may be combined together in any possible combination and may be combined across the various aspects, as appropriate.

The invention will now be further described by the following examples.

EXAMPLES

General Methods

Reactions requiring anhydrous conditions were performed using oven-dried glassware and conducted under a positive pressure of dinitrogen. Anhydrous solvents were prepared in accordance with standard protocols, or alternatively purchased from Aldrich in Sure/Seal™ bottles. Infrared spectra were recorded on a Nicolet Avatar 370DTGS FT-IR spectrometer with internal calibration. $^1$H, $^{13}$C and COSY NMR spectra were recorded on a Bruker Avance 300 spectrometer with residual protic solvent as an internal reference. $^{19}$F NMR were recorded on a Jeol λ 500 MHz spectrometer with CFCl$_3$ as an external reference. Elemental analyses were carried out at London Metropolitan University. Mass spectra and accurate masses were recorded at the EPSRC Mass Spectrometry Service, Swansea. Melting points were recorded on a Gallenkamp MF-370 melting point apparatus and are uncorrected.

Example 1

Synthesis of (4-((2,5-Dioxopyrrolidin-1-yloxy)carbonyl)phenyl)(thiophen-2-yl)iodonium trifluoroacetate (4)

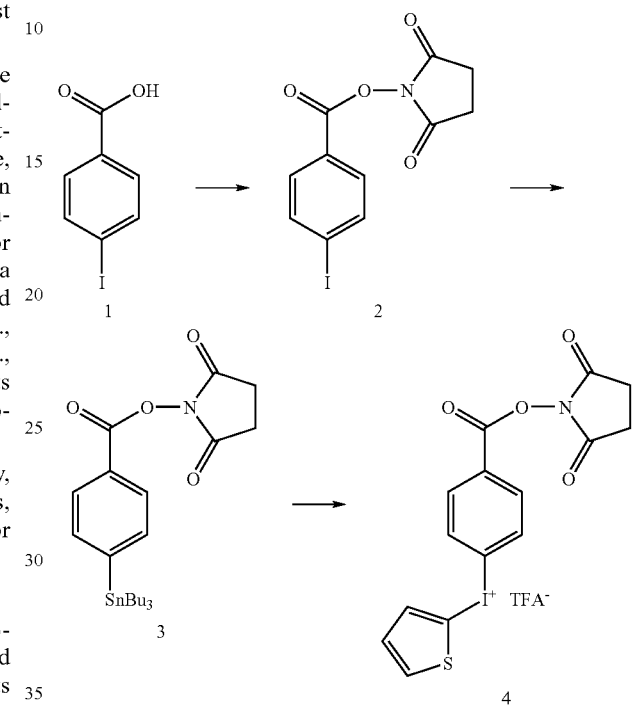

(a) N-Succinimidyl-4-iodobenzoate (2)

To the solution of 4-iodobenzoic acid (1)(1.24 g, 5.0 mmol) and triethylamine (0.71 mL, 5.0 mmol) in DMF (30 mL) was added TSTU (1.51 g, 5.0 mmol). The solution was stirred at room temperature for 2 hours. The reaction was quenched by addition of 10% HCl (50 mL). The precipitate was collected by filtration, washed with water and dried in vacuo to yield the title compound (2) as a white powder (1.42 g, 82%); m.p. 130-132° C.; $v_{max}$/cm$^{-1}$(neat) 1769 (C=O, ester), 1719 (C=O, amide); (Found C, 38.40; H, 2.41; N, 4.15. C$_{11}$H$_8$INO$_4$ requires C, 38.28; H, 2.34; N, 4.06%.); $\delta_H$ (300 MHz, CDCl$_3$) 7.92 (2H, d, J 12.0 Hz, H$_{2/6}$), 7.85 (2H, d, J 12.0 Hz, H$_{3/5}$), 2.92 (4H, s, CH$_2$); $\delta_c$ (75 MHz, CDCl$_3$) 169.0 (OCO), 162.0 (NCO), 138.7 (C$_{2/6}$), 132.0(C$_{3/5}$), 125.3 (C$_1$), 103.3(C$_4$), 26.0 (CH$_2$); m/z (E.I.), 345 (M$^+$, 5%), 231 (100%), 202 (20%), and 76 (48%); HRMS for C$_{11}$H$_8$INO$_4$ requires 344.9493 found 344.9493.

(b) N-Succinimidyl-4-tributylstannyl benzoate (3)

A solution of N-succinimidyl-4-iodobenzoate (2)(1.42 g, 4.1 mmol) and bis(tributyltin) (4.0 mL, 8.2 mmol) in anhydrous N,N-dimethylformamide/toluene (1:1, 70 mL) was degassed with nitrogen for 15 minutes before the addition of Pd(PPh$_3$)$_4$ (56 mg, 0.1 mmol). The solution was refluxed for 24 hours under nitrogen. The reaction was quenched by addition of water (100 mL). The mixture was extracted with diethyl ether (3×50 mL) and the combined organic phases were dried over MgSO$_4$. The solvents were removed in vacuo and the crude material was purified by column chromatography on silica, eluting with hexane and diethyl ether (3:2 then 2:3) to yield the title compound as a colourless oil (1.01 g, 48%); (Found C, 54.28; H, 6.90; N, 2.68. C$_{23}$H$_{35}$NO$_4$Sn requires C, 54.35; H, 6.94; N, 2.76%.); v$_{max}$/cm$^{-1}$(neat) 2922 (C—H), 1769 (O=CO), 1739 (O=CN); δ$_H$ (300 MHz, CDCl$_3$) 8.05 (2H, d, J 9.0 Hz, H$_{2/6}$), 7.67 (2H, d, J 9.0 Hz, H$_{3/5}$), 2.93 (4H, s, COCH$_2$×2), 1.69-1.44 (6H, m, SnCH$_2$CH$_2$), 1.40-1.33 (6H, m, CH$_2$CH$_3$), 1.18-1.12 (6H, m, SnCH$_2$), 0.88 (9H, t, J 6.0 Hz, CH$_2$CH$_3$); δ$_c$ (75 MHz, CDCl$_3$) 169.3 (OCO), 162.7 (NCO), 153.4 (C$_1$), 137.1 (C$_{2/6}$), 129.4 (C$_{3/5}$), 125.1 (C$_4$), 29.4 (SnCH$_2$CH$_2$), 27.5 (CH$_2$CH$_3$), 26.0 (COCH$_2$), 13.8 (CH$_2$CH$_2$CH$_3$), 10.2 (SnCH$_2$); m/z (E.I.), 523 (M$^+$, 32%), 304 (14%), 237 (32%), 101 (100%), 84 (66%), and 72 (65%); HRMS for C$_{23}$H$_{35}$NO$_4{}^{116}$Sn requires 523.1922 found 523.1919.

(c) (4-((2,5-Dioxopyrrolidin-1-yloxy)carbonyl)phenyl)(thiophen-2-yl)iodonium trifluoroacetate (4)

To a solution of diacetoxyiodo-2-thiophene (0.72 g, 2.0 mmol) in anhydrous dichloromethane (25 mL) was added trifluoro acetic acid (0.31 mL, 4.0 mmol) dropwise at −30° C. under nitrogen. After 30 minutes, the solution was warmed to room temperature and stirred for another hour. When the solution was recooled to 30° C., ethyl 4-tributylstannanyl (1.01 g, 2.0 mmol) was added. The solution was warmed to room temperature overnight. The solvent was removed in vacuo and the crude material was purified by recrystallisation from acetonitrile to yield the title compound (4) as colourless needles (0.37 g, 26%); m.p. 106-108° C.; (Found C, 37.84; H, 2.04; N, 2.50. C$_{17}$H$_{151}$F$_3$INO$_6$S requires C, 37.73; H, 2.05; N, 2.59%.); v$_{max}$/cm$^{-1}$(neat) 1732 (ester), 1645 (amide); δ$_H$ (300 MHz, DMF-d$_7$) 8.60 (2H, d, J 9.0 Hz, H$_{2/6}$), 8.25 (2H, d, J 9.0 Hz, H$_{3/5}$), 8.22 (1H, dd, J 6.0 Hz, J' 3.0 Hz, H'$_5$), 8.06 (1H, d, J 3.0 Hz, J''9.0 Hz, H'$_3$), 7.26 (1H, d, J 6.0 Hz, J' 9.0 Hz, H'$_4$), 2.97 (4H, s, 2×CH$_2$); δ$_c$ (125 MHz, DMF-d$_7$) 170.2 (OCO), 162.0 (OCN), 141.0 (C'$_5$), 137.4 (C'$_3$), 135.7 (C$_{2/6}$), 132.6 (C$_{3/5}$), 129.8 (C'$_4$), 127.8 (C$_4$), 127.2 (C$_1$), 102.6 (C'$_2$), 26.0 (CH$_2$); m/z (ES.I.), 429 (MH$^+$, 12%), 428 (M$^+$, 100%), and 331 (7%); HRMS for C$_{15}$H$_{11}$INO$_4$S$^+$ requires 427.9448 found 427.9444.

Example 2

Synthesis of N-succinimidyl-4-fluorobenzoate (5)

To a mixture of CsF (7 mg, 0.05 mmol), TEMPO (1 mg, 10 mol %) and iodonium salt (0.05 mmol) in anhydrous N,N-dimethylformamide (3 mL) and the internal standard 3-trifluoromethyl anisole (0.05 mL, 1 mmol/mL in dry DMF) were added in a long glass tube flushed with nitrogen. The solution was heated at 130° C. for 1.5 hours under nitrogen. When the mixture was cooled to room temperature, a sample (0.3 mL) was taken and diluted with N,N-dimethylformamide (0.4 mL) and analysed by $^{19}$F NMR.

|  | Temperature (° C.) | | | |
| --- | --- | --- | --- | --- |
|  | 70 | 90 | 110 | 130 |
| Yield CsF(1.0 equiv.) | trace | 7% | 10% | 6% |

Example 3

Synthesis of N-succinimidyl-4-[$^{18}$F]fluorobenzoate (5')

NCA [$^{18}$F]fluoride was automatically dried by azeotropic evaporation at 110° C. using a solution of K$_2$CO$_3$ (3 mg, 26 μmol) and Kryptofix$_{2.2.2}$ (16 mg, 42 μmol) in acetonitrile/water (6.5:1) under argon and then redissolved in anhydrous acetonitrile (0.5 mL). An aliquot (~100 MBq) was taken and the acetonitrile was evaporated manually at 110° C. under argon to which a solution of the iodonium salt (4)(2.7 mg, 5 μmol) and TEMPO (1 mg) in DMF (0.1 mL) was added. The reaction was heated at 130° C. for 5 minutes. The reaction was quenched by addition of water (50 μL). An aliquot (20 μL) was taken and analysed by reversed-phase radio HPLC (Phenomenex PolymerX, 50 mm) using 2 mL/min acetonitrile/water (25/75) as eluent and radiochemical yields were also determined by radio-HPLC 4-23% (n=8).

Example 4

(a) (4-((2,5-Dioxopyrrolidin-1-yloxy)carbonyl)phenyl)(4-methoxyphenyl)iodonium trifluoroacetate (6)

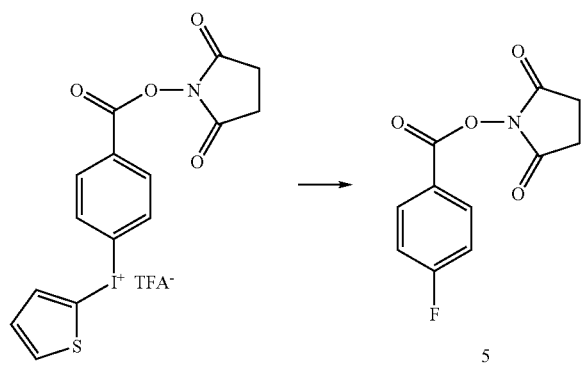

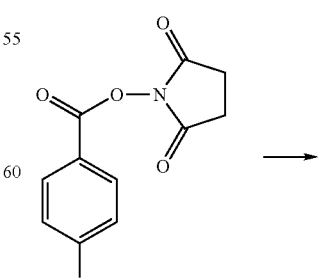

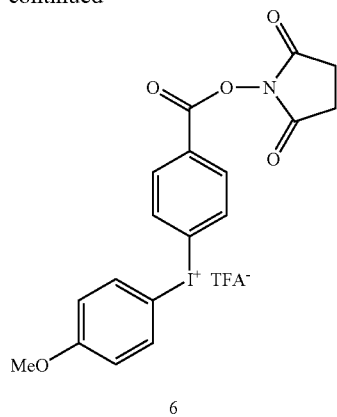

6

To a solution of diacetoxyiodo-4-methoxybenzene (0.64 g, 1.8 mmol) in anhydrous dichloromethane (25 mL) was added trifluoro acetic acid (0.28 mL, 3.6 mmol) dropwise at −30° C. under nitrogen. After 30 minutes, the solution was warmed to room temperature and stirred for another hour. When the solution was recooled to −30° C., N-succinimidyl-4-tributyl-stannyl benzoate (3)(0.93 g, 1.8 mmol) was added. The solution was warmed to room temperature overnight. The solvent was removed in vacuo and the crude material was purified by column chromatography on silica, eluting with dichloromethane and methanol (15:1) and then recrystallisation from dichloromethane and petrol to yield the title compound (6) as colourless needles (0.38 g, 37%); m.p. 102-103° C.; (Found C, 42.56; H, 2.74; N, 2.38. $C_{20}H_{15}F_3INO_7$ requires C, 42.50; H, 2.67; N, 2.48%.); $v_{max}/cm^{-1}$(neat) 1734 (ester), 1654 (amide); $\delta_H$(500 MHz, DMSO-$d_6$) 8.40 (2H, d, J 9.0 Hz, $H_{3/5}$), 8.23 (2H, d, J 9.0 Hz, $H'_{3/5}$), 8.16 (1H, d, J 9.0 Hz, $H_{2/6}$), 7.11 (2H, d, J 9.0 Hz, $H'_{2/6}$), 3.81 (3H, s, $CH_3$), 2.84 (4H, s, $CH_2CH_2$); $\delta_c$(125 MHz, CDCl$_3$) 169.9 (OCO), 163.6 (OCN), 161.0 ($C'_4$), 137.9 ($C'_{2/6}$), 134.9 ($C_{3/5}$), 133.3 ($C'_{3/5}$), 128.8 ($C_4$), 123.1($C_1$), 118.5 ($C_{2/6}$), 104.2 ($C'_1$), 56.0 (OCH$_3$), 26.0 (CH$_2$); m/z (ES.I.), 452 (M$^+$, 100%), 369 (20%), 355 (60%), and 341 (23%); HRMS for $C_{18}H_{15}INO_5^+$ requires 451.9989 found 451.9987.

(b) (4-((2,5-Dioxopyrrolidin-1-yloxy)carbonyl)phenyl)(2-methoxyphenyl)iodonium trifluoroacetate (7)

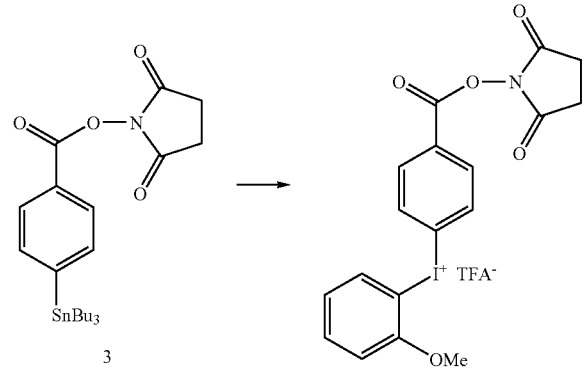

7

To a solution of diacetoxyiodo-2-methoxybenzene (0.77 g, 2.2 mmol) in anhydrous dichloromethane (25 mL) was added trifluoro acetic acid (0.33 mL, 4.4 mmol) dropwise at −30° C. under nitrogen. After 30 minutes, the solution was warmed to room temperature and stirred for another hour. When the solution was recooled to −30° C., N-succinimidyl-4-tributyl-stannyl benzoate (3)(1.11 g, 2.2 mmol) was added. The solution was warmed to room temperature overnight. The solvent was removed in vacuo and the crude material was purified by column chromatography on silica, eluting with dichloromethane and methanol (12:1) to yield the title compound (7) as colourless needles (0.44 g, 36%); m.p. 142-144° C.; (Found C, 42.57; H, 2.68; N, 2.37. $C_{20}H_{15}F_3INO_7$ requires C, 42.50; H, 2.67; N, 2.48%.); $v_{max}/cm^{-1}$(neat) 1660 (ester), 1632 (amide); $\delta_H$(300 MHz, DMSO-$d_6$) 8.33 (1H, d, J 9.0 Hz, $H'_3$), 8.15 (2H, d, J 6.0 Hz, $H_{3/5}$), 7.66 (1H, t, J 9.0 Hz, $H'_5$), 7.50 (2H, d, J 6.0 Hz, $H_{2/6}$), 7.32 (1H, d, J 9.0 Hz, $H'_6$), 7.10 (1H, t, J 9.0 Hz, $H'_4$), 3.94 (3H, s, $CH_3$), 2.97 (2H, s, $CH_2$), 2.82 (2H, s, $CH_2$); $\delta_c$(125 MHz, CDCl$_3$) 169.0 (OCO), 169.0 (OCN), 157.0 ($C'_2$), 140.3 ($C_4$), 137.9 ($C'_3$), 135.6 ($C_{3/5}$), 135.5 ($C'_5$), 130.3 ($C_{2/6}$), 124.0 ($C'_4$), 117.0 ($C_1$), 118.5 ($C'_6$), 107.3 ($C'_1$), 57.6 (OCH$_3$), 39.8 (CH$_2$), 34.9 (CH$_2$); m/z (ES.I.), 452 (M$^+$, 20%), 227 (92%), 133 (100%), 92 (65%), and 60 (57%); HRMS for $C_{18}H_{15}INO_5^+$ requires 451.9989 found 451.9984.

Example 5

[4-(2,5-Dioxo-pyrrolidin-1-yloxycarbonyl)-phenyl]-phenyl-iodonium trifluoroacetate (8)

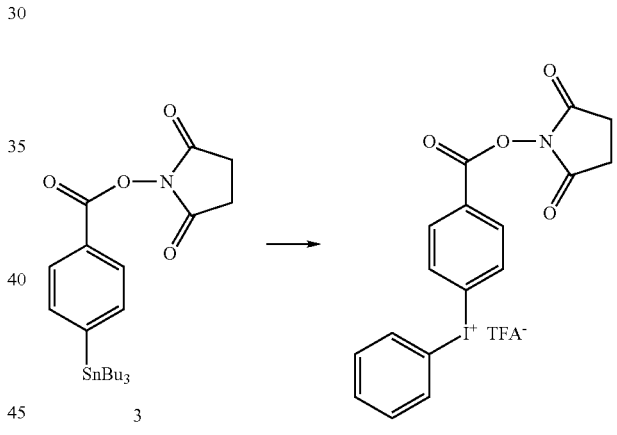

8

To a solution of diacetoxyiodo-4-methoxybenzene (2.03 g, 4.0 mmol) in anhydrous dichloromethane (40 mL) was added trifluoro acetic acid (0.62 mL, 8.0 mmol) dropwise at −30° C. under nitrogen. After 30 minutes, the solution was warmed to room temperature and stirred for another hour. When the solution was recooled to −30° C., N-succinimidyl-4-tributyl-stannyl benzoate (3)(2.03 g, 4.0 mmol) was added. The solution was warmed to room temperature overnight. The solvent was removed in vacuo and the crude material was purified by column chromatography on silica, eluting with dichloromethane and methanol (20:1) and then recrystallisation from dichloromethane and petrol to yield the title compound (8) as colourless needles (0.40 g, 20%); m.p. 95-97° C.; (Found C, 43.87; H, 2.49; N, 2.66. $C_{19}H_{13}F_3INO_6$ requires C, 43.95; H, 2.52; N, 2.70%.); $v_{max}/cm^{-1}$(neat) 1736 (ester), 1650 (amide); $\delta_H$(300 MHz, DMSO-$d_6$) 8.48 (2H, d, J 9.0 Hz, $H_{3/5}$), 8.30 (2H, d, J 6.0 Hz, $H'_{2/6}$), 8.19 (2H, d, J 9.0 Hz, $H_{2/6}$), 7.69 (1H, t, J 6.0 Hz, $H'_4$), 7.55 (2H, t, J 6.0 Hz, $H'_{3/5}$), 2.89 (4H, s, CH$_2$); $\delta_c$ (125 MHz, CDCl$_3$) 169.0 (OCO), 161.0

(OCN), 135.6 (C'$_{2/6}$), 135.4 (C$_{2/6}$), 133.3 (C$_{3/5}$), 132.7 (C'$_{3/5}$), 130.5 (C$_4$), 129.0 (C'$_4$), 123.1 (C$_1$), 116.6 (C'$_1$), 26.5 (CH$_2$); m/z (ES.I.), 422 (M$^+$, 60%), 325 (100%), and 198 (10%); HRMS for C$_{17}$H$_{13}$INO$_4^+$ requires 421.9884 found 421.9884.

Under the reaction conditions of Example 2 above, trace amounts of N-succinimidyl-4-fluorobenzoate (5) were produced.

Example 6

Synthesis of (4-((2,5-Dioxopyrrolidin-1-yloxy)carbonyl)phenyl)(thiophen-2-yl)iodonium trifluoroacetate (12)

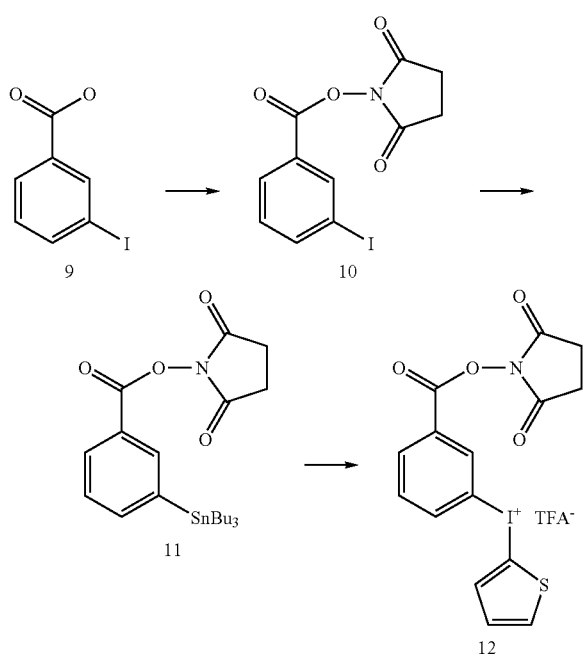

(a) N-Succinimidyl-3-iodobenzoate (10)

To the solution of 3-iodobenzoic acid (9)(4.42 g, 17.8 mmol) and triethylamine (2.53 mL, 17.8 mmol) in DMF (80 mL) was added TSTU (5.38 g, 17.8 mmol). The solution was stirred at room temperature for 4 hours. The reaction was quenched by addition of 10% HCl (150 mL). The precipitate was collected by filtration, washed with water and dried in vacuo to yield the title compound (10) as a white powder (4.20 g, 69%); $v_{max}$/cm$^{-1}$(neat) 1770 (C=O, ester), 1728 (C=O, amide); (Found C, 38.37; H, 2.26; N, 4.08. C$_{11}$H$_8$INO$_4$ requires C, 38.28; H, 2.34; N, 4.06%.); $\delta_H$ (300 MHz, CDCl$_3$) 8.35 (1H, s, H$_2$), 8.21 (1H, d, J 9.0 Hz, H$_6$), 8.11 (1H, d, J 6.0 Hz, H$_4$), 7.46 (1H, dd, J 9.0 Hz, J'6.0 Hz, H$_5$), 2.90 (4H, s, CH$_2$); $\delta_c$ (75 MHz, CDCl$_3$) 170.2 (OCO), 160.9 (NCO), 144.3 (C$_4$), 138.2 (C$_2$), 131.8 (C$_5$), 129.6 (C$_6$), 127.1 (C$_1$), 95.3 (C$_3$), 26.0 (CH$_2$); m/z (E.I.), 345 (M$^+$, 10%), 231 (100%), 202 (30%), and 76 (68%); HRMS for C$_{11}$H$_8$INO$_4$ requires 344.9493 found 344.9495.

(b) N-Succinimidyl-3-tributylstannyl benzoate (11)

A solution of N-succinimidyl-3-iodobenzoate (10)(4.00 g, 11.6 mmol) and bis(tributyltin) (11.3 mL, 23.2 mmol) in anhydrous N,N-dimethylformamide/toluene (1:1, 140 mL) was degassed with nitrogen for 15 minutes before the addition of Pd(PPh$_3$)$_4$ (158 mg, 0.3 mmol). The solution was refluxed for 24 hours under nitrogen. The reaction was quenched by addition of water (150 mL). The mixture was extracted with diethyl ether (3×50 mL) and the combined organic phases were dried over MgSO$_4$. The solvents were removed in vacuo and the crude material was purified by column chromatography on silica, eluting with hexane and diethyl ether (3:2) to yield the title compound as a colourless oil (2.74 g, 46%); (Found C, 54.30; H, 6.91; N, 2.72. C$_{23}$H$_{35}$NO$_4$Sn requires C, 54.35; H, 6.94; N, 2.76%.); $v_{max}$/cm$^{-1}$(neat) 2922 (C—H), 1770 (O=CO), 1740 (O=CN); $\delta_H$ (300 MHz, CDCl$_3$) 8.22 (1H, s, H$_2$), 8.07 (1H, d, J 6.0 Hz, H$_6$), 7.78 (1H, d, J 6.0 Hz,), 7.49 (1H, t, J 6.0 Hz, H$_5$), 2.94 (4H, s, COCH$_2$×2), 1.60-1.50 (6H, m, SnCH$_2$CH$_2$), 1.40-1.31 (6H, m, CH$_2$CH$_3$), 1.16-1.08 (6H, m, SnCH$_2$), 0.86 (9H, t, J 6.0 Hz, CH$_2$CH$_3$); $\delta_c$ (75 MHz, CDCl$_3$) 169.2 (OCO), 162.8 (NCO), 144.05 (C$_1$), 143.1 (C$_2$), 138.5 (C$_6$), 130.3 (C$_4$), 128.3 (C$_5$), 125.2 (C$_3$), 29.4 (SnCH$_2$CH$_2$), 27.6 (CH$_2$CH$_3$), 26.1 (COCH$_2$), 13.5 (CH$_2$CH$_2$CH$_3$), 10.2 (SnCH$_2$); m/z (E.I.), 523 (M$^+$, 40%), 304 (30%), 101 (100%), and 72 (65%); HRMS for C$_{23}$H$_{35}$NO$_4$$^{116}$Sn requires 523.1922 found 523.1920.

(c) (3-((2,5-Dioxopyrrolidin-1-yloxy)carbonyl)phenyl)(thiophen-2-yl)iodonium trifluoroacetate (12)

To a solution of diacetoxyiodo-2-thiophene (1.86 g, 5.60 mmol) in anhydrous dichloromethane (50 mL) was added trifluoro acetic acid (0.80 mL, 10.32 mmol) dropwise at −30° C. under nitrogen. After 30 minutes, the solution was warmed to room temperature and stirred for another hour. When the solution was recooled to 30° C., ethyl 3-tributylstannanyl benzoate (2.62 g, 5.16 mmol) was added. The solution was warmed to room temperature overnight. The solvent was removed in vacuo and the crude material was purified by column chromatography on silica, eluting with dichloromethane and methanol (15:1) and then recrystallised from acetonitrile to yield the title compound as colourless needles (0.89 g, 32%); m.p. 118-120° C.; (Found C, 37.64; H, 2.08; N, 2.51. C$_{17}$H$_{151}$F$_3$INO$_6$S requires C, 37.73; H, 2.05; N, 2.59%.); $v_{max}$/cm$^{-1}$(neat) 1732 (ester), 1661 (amide); $\delta_H$(300 MHz, DMSO-d$_6$) 8.97 (1H, s, H$_2$), 8.64 (1H, d, J 6.0 Hz, H$_6$), 8.32 (1H, d, J 6.0 Hz,), 8.14 (1H, d, J 9.0 Hz, H$_1$'), 7.99 (1H, d, J 6.0 Hz, H$_4$'), 7.80 (1H, t, J 6.0 Hz, H$_5$), 7.20 (1H, dd, J 9.0 Hz, J'6.0 Hz, H$_3$'), 2.92 (4H, s, COCH$_2$×2); $\delta_c$ (75 MHz, DMSO-d$_6$) 170.1 (OCO), 160.7 (NCO), 141.2 (C$_1$), 141.0 (C$_2$), 137.8 (C$_6$), 135.7 (C$_2$'), 135.2 (C$_4$), 133.8 (C$_4$'), 132.2 (C$_3$'), 127.5 (C$_5$), 120.4 (C$_1$'), 101.6 (C$_3$), 26.0 (COCH$_2$); m/z (ES.I.), 429 (MH$^+$, 20%), 428 (M$^+$, 100%), and 331 (45%); HRMS for C$_{15}$H$_{11}$INO$_4$S$^+$ requires 427.9448 found 427.9447.

Under the reaction conditions of Example 2 above, trace amounts of N-succinimidyl-3-fluorobenzoate were produced.

The invention claimed is:

1. An iodonium compound of formula (I):

where R$^{AR1}$ is a phenyl group, bearing at least one acylamidocarboxy substituent;

$R^{AR2}$ is a C5-10 aryl group, optionally substituted by one or more groups selected from the group consisting of $C_{1-12}$ alkyl, $C_{5-12}$ aryl, $C_{3-12}$ heterocyclyl, ether, thioether, nitro, cyano, amine, and halo, and may be linked to a solid support or fluorous tag; and X is a counteranion.

2. The compound according to claim 1, wherein $R^{AR1}$ bears a single substituent which is succinimidylcarboxy.

3. The compound according to claim 1, wherein X is selected from the group consisting of $CF_3COO$, TsO, MsO, NsO, TfO, $BAr_4$, $NO_3$, Br, Cl and $HSO_4(-)$, where Ar represents a $C_{5-20}$ aryl group.

4. The compound according to claim 3, wherein X is $CF_3COO$.

5. The compound according to claim 1, wherein $R^{AR2}$ is a thiophenyl or furanyl.

6. The compound according to claim 5, wherein $R^{AR2}$ is thiophen-2-yl.

7. The compound according to claim 6, wherein the thiophen-2-yl is unsubstituted.

8. The compound according to claim 1, wherein $R^{AR2}$ is phenyl.

9. The compound according to claim 1, wherein the optional substituents for $R^{AR2}$ are selected from the group consisting of ether, thioether and amine.

10. A method of synthesising a compound of formula II:

(II)

comprising fluoridating a compound of formula I of claim 1.

11. The method according to claim 10, wherein the fluoridation is carried out by reacting the compound of formula I with a source of fluoride selected from NaF, KF, CsF, tetraalkylammonium fluoride, or tetraalkylphosphonium fluoride.

12. The method according to claim 11, wherein a phase transfer catalyst is used in addition to the source of fluoride.

13. The method according to claim 11, wherein a free radical trap is also used.

14. A method of synthesising a compound of formula I of claim 1 comprising the step of reacting a compound of formula IIIa or IIIb:

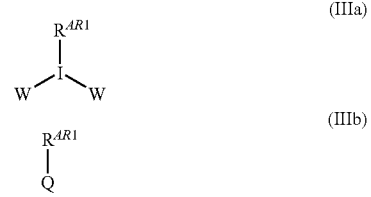

with a compound of formula IVa or IVb:

wherein Q is $SNR_3$, $B(OH)_2$ or $B(OR)_2$, where R is C1-7 alkyl; and

W is OCORW or halo, where RW is C1-4 alkyl.

* * * * *